United States Patent [19]

Wollweber et al.

[11] Patent Number: 4,927,844
[45] Date of Patent: May 22, 1990

[54] N-SUBSTITUTED DICHLOROMALEIMIDES, AND ANTI-BACTERIAL AND FUNGICIDAL USE THEREOF

[75] Inventors: Detlef Wollweber, Wuppertal; Wolfgang Krämer, Burscheid; Wilhelm Brandes, Leichlingen; Stefan Dutzmann, Duesseldorf; Gerd Hanssler, Leverkusen, all of Fed. Rep. of Germany

[73] Assignee: Bayer Aktiengesellschaft, Leverkusen, Fed. Rep. of Germany

[21] Appl. No.: 269,938

[22] Filed: Nov. 10, 1988

[30] Foreign Application Priority Data

Nov. 13, 1987 [DE] Fed. Rep. of Germany ....... 3738591

[51] Int. Cl.$^5$ ................. C07D 207/452; A01N 37/30
[52] U.S. Cl. ..................................... 514/425; 548/546
[58] Field of Search ......................... 514/425; 548/546

[56] References Cited

U.S. PATENT DOCUMENTS

| | | | |
|---|---|---|---|
| 3,129,225 | 4/1964 | Shapiro | 260/247.2 |
| 3,624,080 | 11/1971 | Dimroth et al. | 544/14 |
| 3,894,043 | 7/1975 | Moser et al. | 548/546 |
| 4,582,849 | 4/1986 | Marzolph et al. | 514/425 |

FOREIGN PATENT DOCUMENTS

| | | |
|---|---|---|
| 0045907 | 2/1982 | European Pat. Off. . |
| 0098953 | 1/1984 | European Pat. Off. . |
| 0117482 | 9/1984 | European Pat. Off. . |
| 3314249 | 10/1984 | Fed. Rep. of Germany . |
| 617320 | 5/1980 | Switzerland . |
| 880555 | 10/1961 | United Kingdom . |
| 2087879 | 6/1982 | United Kingdom . |

OTHER PUBLICATIONS

Riedel-Dehaen Laborchemikalien 1984, Gultig ab 19.Marz 1984, Chemikalien fur Analyse und Synthese in Labor und Betrieb, pp. 37–39, 41, 43, 398, 403, 408, 874, A43, A44.
Heterocycles, vol. 108, 1988 Synthesis and Structure of N–Substituted Dichloromaleimides, pp. 719–720.
Wilen et al., Benzene, its Derivatives, and Condensed Benzenoid Compounds, vol. 102, 1985, p. 571.
Benzenes, vol. 100, 1984, Pharm. Suec. 1983, p. 589.

Primary Examiner—David B. Springer
Attorney, Agent, or Firm—Sprung Horn Kramer & Woods

[57] ABSTRACT

New N-substituted dichloromaleimides of the general formula (I)

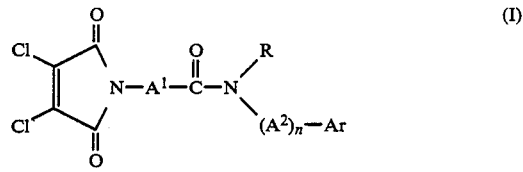

in which
R stands for hydrogen or alkyl
Ar stands for optionally substituted aryl,
$A^1$ and $A^2$ independently of one another each stand for optionally substituted alkylene and
n stands for a number 0 or 1, with the exception of the compound 2-(dichloromaleimido)acetanilide, have been found. These compounds are useful as pesticides, especially as fungicides and bactericides.

10 Claims, No Drawings

N-SUBSTITUTED DICHLOROMALEIMIDES, AND ANTI-BACTERIAL AND FUNGICIDAL USE THEREOF

The invention relates to new N-substituted dichloromaleimides, a process to the preparation thereof, and their use as pesticides.

It is known that certain dicarboximides, such as, for example, the compound N-trichloromethanesulphenylphthalimides (folpet) or the compound N-trichloromethanesulphenyl-tetrahydrophthalimide (captan) have a good fungicidal activity (cf., for example, K. H. Büchel, "Pflanzenaschutz and Schädlingsbekämpfung" [Plant Protection and Pest Control], p. 140, Thieme Verlag Stuttgart 1977).

However, the activity of these known compounds is not completely satisfactory in all fields of applications, in particular at low application rates and concentrations.

Furthermore, the compound 2-(dichloromaleimidoacetanilide has been disclosed (cf. FR 2,005,669). Nothing was known hitherto about an activity of this compound against pests.

New N-substituted dichloromaleimides of the general formula (I)

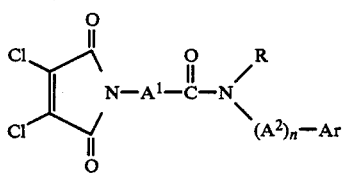

in which
R stands for hydrogen or alkyl,
Ar stands for optionally substituted aryl,
$A^1$ and $A^2$ independently of one another each stand for optionally substituted alkylene and
n stands for a number 0 or 1,
with the exception of the compound 2-(dichloromaleimido)-acetanilide, have been found.

Depending on the type of the substituents $A^1$ and/or $A^2$, the compounds of the formula (I) may be present as optical isomers or isomer mixtures of varying composition. Both the pure isomers and the isomer mixtures are claimed according to the invention.

Furthermore, it has been found that the new N-substituted dichloromaleimides of the general formula (I)

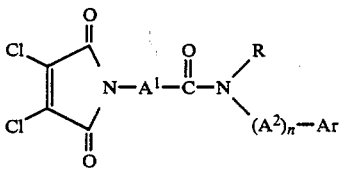

in which
R stands for hydrogen or alkyl,
Ar stands for optionally substituted aryl,
$A^1$ and $A^2$ independently of one another each stand for optionally substituted alkylene and
n stands for a number 0 or 1,
with the exception of the compound 2-(dichloromaleimido)-acetanilide, are obtained when dichloromaleimidocarbonyl halides of the formula (II)

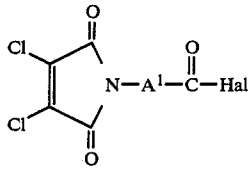

in which
$A^1$ has the abovementioned meaning and
Hal stands for halogen,
are reacted with amines of the formula (III)

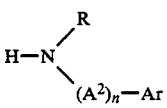

in which
R, Ar, $A^2$ and n have the abovementioned meaning, if appropriate in the presence of a diluent and if appropriate in the presence of an acid-binding agent.

Finally, it has been found that the new N-substituted dichloromaleimides of the general formula (I) have a good action against pests.

Surprisingly, the N-substituted dichloromaleimides of the formula (I) according to the invention show a considerably better fungicidal activity than the dicarboximides known from the prior art, such as, for example, the compound N-trichloromethanesulphenylphthalimide (folpet) or the compound N-trichloromethanesulphenyl-tetrahydrophthalimide (captan), which are chemically similar compounds of a similar type of action.

Formula (I) provides a general definition of the N-substituted dichloromaleimides according to the invention. Preferred compounds of the formula (I) are those in which
R stands for hydrogen or for straight-chain or branched alkyl having 1 to 6 carbon atoms,
Ar stands for phenyl which is optionally monosubstituted or polysubstituted by identical or different substituents, suitable substituents being: halogen, cyano, nitro, in each case straight-chain or branched alkyl, alkoxy or alkylthio, each having 1 to 4 carbon atoms, in each case straight-chain or branched halogenoalkyl, halogenoalkoxy, dioxyhalogenoalkylene or halogenoalkylthio, each having 1 to 4 carbon atoms and 1 to 9 identical or different halogen atoms, in each case straight-chain or branched alkenyl, alkinyl, alkenyloxy or alkinyloxy, each having 3 to 6 carbon atoms, cycloalkyl having 3 to 7 carbon atoms, in each case straight-chain or branched alkoxycarbonylalkyl or alkoxyalkyl, each having 1 to 4 carbon atoms in the individual alkyl moieties, or phenyl, benzyl, phenoxy or benzyloxy, each optionally monosubstituted or polysubstituted by identical or different substituents from the series comprising halogen and/or straight-chain or branched alkyl having 1 to 4 carbon atoms,
$A^1$ and $A^2$ independently of one another each stand for optionally phenyl-substituted, straight-chain or branched alkylene having 1 to 8 carbon atoms, where the phenyl substituent can optionally be monosubstituted or polysubstituted by identical or different substituents from the series comprising:

halogen, in particular fluorine, chlorine or bromine, in each case straight-chain or branched alkyl, alkoxy, halogenoalkyl or halogenoalkoxy, each having 1 to 4 carbon atoms, and, in the case of halogenoalkyl or halogenoalkoxy, having 1 to 9 identical or different halogen atoms, and n stands for a number 0 or 1, with the exception of the compound 2-(dichloromaleimido)-acetanilide.

Very particularly preferred compounds of the formula (I) are those in which

R stands for hydrogen or for straight-chain or branched alkyl having 1 to 4 carbon atoms, Ar stands for phenyl which is optionally monosubstituted to pentasubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, dioxydifluoromethylene, trifluoromethylthio, allyl, propargyl, cyclopropyl, cyclohexyl, phenyl, benzyl, phenoxy or benzyloxy, $A^1$ stands for straight-chain or branched alkylene which is optionally monosubstituted by phenyl and which has 1 to 6 carbon atoms, $A^2$ stands for unsubstituted straight-chain or branched alkylene having 1 to 6 carbon atoms and n stands for a number 0 or 1, with the exception of the compound 2-(dichloromaleimido)-acetanilide.

Very particularly preferred compounds of the formula (I) are those in which

R stands for hydrogen, methyl or ethyl,

Ar stands for phenyl which is optionally monosubstituted, disubstituted or trisubstituted by identical or different substituents, suitable substituents being: fluorine, chlorine, bromine, cyano, nitro, methyl, ethyl, n- or i-propyl, n-, i-, s- or t-butyl, methoxy, methylthio, trifluoromethyl, trifluoromethoxy, trifluoromethylthio or divalent dioxydifluoromethylene, $A^1$ stands for straight-chain or branched alkylene which is optionally monosubstituted by phenyl and which has 1 to 4 carbon atoms, $A^2$ stands for straight-chain or branched alkylene having 1 to 4 carbon atoms and n stands for a number 0 or 1, with the exception of the compound 2-(dichloromaleimido)-acetanilide.

In addition to the compounds mentioned in the preparation examples, the following N-substituted dichloromaleimides of the general formula (I) may be mentioned individually:

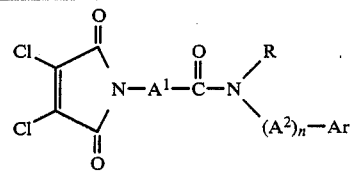

| $A^1$ | R | $(A^2)_n$ | Ar |
|---|---|---|---|
| $-CH_2-$ | H | — | $F_3C-$C$_6$H$_3-$CF$_3$ |
| $-CH_2$ | H | — | benzodioxole-CF$_2$ |
| $-CH_2-$ | H | $-CH_2-$ | $-C_6H_4-CF_3$ |
| $-CH_2-$ | H | $-(CH_2)_4-$ | $-C_6H_4-Cl$ |
| $-CH_2-$ | H | $-(CH_2)_6-$ | $-C_6H_4-Cl$ |
| $-CH_2-$ | H | $-CH_2-$ | $F_3C-$C$_6$H$_3-$OCF$_3$ |
| $-CH_2-$ | H | $-CH_2-$ | 2,4-Cl$_2$-C$_6$H$_3-$ |
| $-CH_2-$ | H | $-(CH_2)_3-$ | $-C_6H_4-Cl$ |
| $-CH_2$ | H | $-(CH_2)_5-$ | $-C_6H_4-Cl$ |
| $-(CH_2)_4-$ | H | — | 2,3-Cl$_2$-C$_6$H$_3-$ |
| $-(CH_2)_4-$ | H | — | $-C_6H_4-Cl$ |

-continued $$\text{(I)}$$

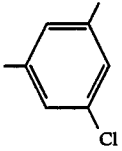

| $A^1$ | R | $(A^2)_n$ | Ar |
|---|---|---|---|
| $-(CH_2)_4-$ | H | — | 3,5-dichlorophenyl |
| $-CH_2-$ | H | — | 4-CF$_3$-phenyl |
| $-CH_2-$ | H | — | 4-OCF$_3$-phenyl |
| $-CH_2-$ | H | — | 2-Cl-5-CH$_3$-phenyl |
| $-CH_2-$ | H | — | 4-F-phenyl |
| $-CH_2-$ | H | — | 3,5-dichlorophenyl |
| $-CH_2-$ | H | — | 4-Cl-3-CF$_3$-phenyl |
| $-CH_2-$ | H | — | 2,3,4-trichlorophenyl |
| $-CH_2-$ | H | — | 4-Cl-3-CH$_3$-phenyl |

-continued $$\text{(I)}$$

| $A^1$ | R | $(A^2)_n$ | Ar |
|---|---|---|---|
| $-CH_2-$ | H | — | 3-Cl-4-CF$_3$-phenyl |
| $-CH_2-$ | H | $-CH_2-$ | 4-OCF$_3$-phenyl |
| $-CH_2-$ | H | $-CH_2-$ | 4-CF$_3$-phenyl |
| $-CH_2-$ | H | $-CH_2-$ | 3-Cl-4-OCF$_3$-phenyl |
| $-CH_2-$ | H | $-(CH_2)_2-$ | 4-CF$_3$-phenyl |
| $-CH_2-$ | H | $-(CH_2)_2-$ | 2-CF$_3$-phenyl |
| $-CH_2-$ | H | $-(CH_2)_2-$ | 4-OCF$_3$-phenyl |
| $-(CH_2)_2-$ | H | — | 4-CF$_3$-phenyl |
| $-(CH_2)_2-$ | H | — | 4-OCF$_3$-phenyl |
| $-(CH_2)_2-$ | H | — | 2-Cl-5-CH$_3$-phenyl |
| $-(CH_2)_2-$ | H | — | 4-F-phenyl |

-continued
$$\text{(I)}$$
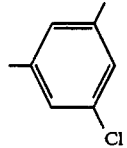
| $A^1$ | R | $(A^2)_n$ | Ar |
|---|---|---|---|
| $-(CH_2)_2-$ | H | — | 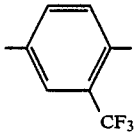 3,5-diCl-C6H3 |
| $-(CH_2)_2-$ | H | — | 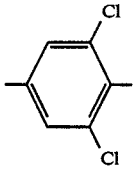 4-Cl-3-CF3-C6H3 |
| $-(CH_2)_2-$ | H | — | 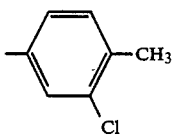 3,4,5-triCl-C6H2 |
| $-(CH_2)_2-$ | H | — | 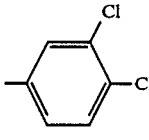 4-CH3-3-Cl-C6H3 |
| $-(CH_2)_2-$ | H | — | 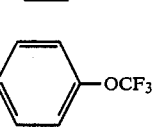 3-Cl-4-CF3-C6H3 |
| $-(CH_2)_2-$ | H | $-CH_2-$ | 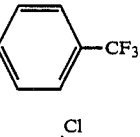 4-OCF3-C6H4 |
| $-(CH_2)_2-$ | H | $-CH_2-$ | 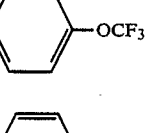 4-CF3-C6H4 |
| $-(CH_2)_2-$ | H | $-CH_2-$ | 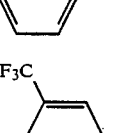 3-Cl-4-OCF3-C6H3 |
| $-(CH_2)_2-$ | H | $-(CH_2)_2-$ | 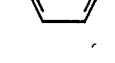 4-CF3-C6H4 |
| $-(CH_2)_2-$ | H | $-(CH_2)_2-$ | 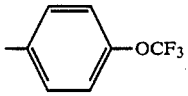 2-CF3-C6H4 |
-continued
$$\text{(I)}$$
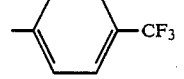
| $A^1$ | R | $(A^2)_n$ | Ar |
|---|---|---|---|
| $-(CH_2)_2-$ | H | $-(CH_2)_2-$ | 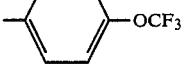 4-OCF3-C6H4 |
| $-(CH_2)_3-$ | H | — | 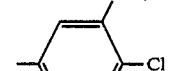 4-CF3-C6H4 |
| $-(CH_2)_3-$ | H | — |  4-OCF3-C6H4 |
| $-(CH_2)_3-$ | H | — | 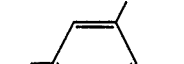 3-CH3-4-Cl-C6H3 |
| $-(CH_2)_3-$ | H | — |  4-F-C6H4 |
| $-(CH_2)_3-$ | H | — | 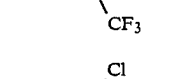 3,5-diCl-C6H3 |
| $-(CH_2)_3-$ | H | — | 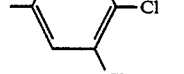 4-Cl-3-CF3-C6H3 |
| $-(CH_2)_3-$ | H | — | 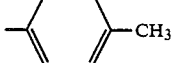 3,4,5-triCl-C6H2 |
| $-(CH_2)_3-$ | H | — | 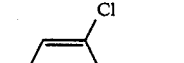 4-CH3-3-Cl-C6H3 |
| $-(CH_2)_3-$ | H | — |  3-Cl-4-CF3-C6H3 |

-continued $$\text{(I)}$$

Structure (I): 3,4-dichloro-1H-pyrrole-2,5-dione with N-A¹-C(=O)-N(R)-(A²)ₙ-Ar substituent

| A¹ | R | (A²)ₙ | Ar |
|---|---|---|---|
| —(CH₂)₃— | H | —CH₂— | 4-OCF₃-phenyl |
| —(CH₂)₃— | H | —CH₂— | 4-CF₃-phenyl |
| —(CH₂)₃— | H | —CH₂— | 3-Cl-4-OCF₃-phenyl |
| —(CH₂)₃— | H | —(CH₂)₂— | 4-CF₃-phenyl |
| —(CH₂)₃— | H | —(CH₂)₂— | 2-CF₃-phenyl |
| —(CH₂)₃— | H | —(CH₂)₂— | 4-OCF₃-phenyl |
| —CH(CH₃)— | H | — | 4-CF₃-phenyl |
| —CH(CH₃)— | H | — | 4-OCF₃-phenyl |
| —CH(CH₃)— | H | — | 2-CH₃-4-Cl-phenyl (2-methyl-4-chloro; Cl at 4, CH₃ at 3) |
| —CH(CH₃)— | H | — | 4-F-phenyl |
| —CH(CH₃)— | H | — | 3,5-diCl-phenyl |
| —CH(CH₃)— | H | — | 4-Cl-3-CF₃-phenyl |
| —CH(CH₃)— | H | — | 3,4,5-triCl-phenyl |
| —CH(CH₃)— | H | — | 3-Cl-4-CH₃-phenyl |
| —CH(CH₃)— | H | — | 3-Cl-4-CF₃-phenyl |
| —CH(CH₃)— | H | —CH₂— | 4-OCF₃-phenyl |
| —CH(CH₃)— | H | —CH₂— | 4-CF₃-phenyl |
| —CH(CH₃)— | H | —CH₂— | 3-Cl-4-OCF₃-phenyl |
| —CH(CH₃)— | H | —(CH₂)₂— | 4-CF₃-phenyl |
| —CH(CH₃)— | H | —(CH₂)₂— | 2-CF₃-phenyl |

-continued $$\text{(I)}$$

Structure: 3,4-dichloro-maleimide-N-A¹-C(=O)-N(R)-(A²)ₙ-Ar

| A¹ | R | (A²)ₙ | Ar |
|---|---|---|---|
| −CH(CH₃)− | H | −(CH₂)₂− | 4-OCF₃-C₆H₄ |
| −C(CH₃)₂− | H | − | 4-CF₃-C₆H₄ |
| −C(CH₃)₂− | H | − | 4-OCF₃-C₆H₄ |
| −C(CH₃)₂− | H | − | 3-CH₃-4-Cl-C₆H₃ |
| −C(CH₃)₂− | H | − | 4-F-C₆H₄ |
| −C(CH₃)₂− | H | − | 3,5-Cl₂-C₆H₃ |
| −C(CH₃)₂− | H | − | 4-Cl-3-CF₃-C₆H₃ |
| −C(CH₃)₂− | H | − | 3,4,5-Cl₃-C₆H₂ |
| −C(CH₃)₂− | H | − | 3-Cl-4-CH₃-C₆H₃ |
| −C(CH₃)₂− | H | − | 3-Cl-4-CF₃-C₆H₃ |
| −C(CH₃)₂− | H | −CH₂− | 4-OCF₃-C₆H₄ |
| −C(CH₃)₂− | H | −CH₂− | 4-CF₃-C₆H₄ |
| −C(CH₃)₂− | H | −CH₂− | 3-Cl-4-OCF₃-C₆H₃ |
| −C(CH₃)₂− | H | −(CH₂)₂− | 4-CF₃-C₆H₄ |
| −C(CH₃)₂− | H | −(CH₂)₂− | 2-CF₃-C₆H₄ |
| −C(CH₃)₂− | H | −(CH₂)₂− | 4-OCF₃-C₆H₄ |
| −CH(CH(CH₃)₂)− | H | − | 4-CF₃-C₆H₄ |
| −CH(CH(CH₃)₂)− | H | − | 4-OCF₃-C₆H₄ |
| −CH(CH(CH₃)₂)− | H | − | 3-CH₃-4-Cl-C₆H₃ |
| −CH(CH(CH₃)₂)− | H | − | 4-F-C₆H₄ |

-continued $$\text{(I)}$$

Structure: 3,4-dichloro-maleimide-N-A¹-C(=O)-N(R)-(A²)ₙ-Ar

| A¹ | R | (A²)ₙ | Ar |
|---|---|---|---|
| -CH-CH(CH₃)₂ | H | — | 3,5-dichlorophenyl |
| -CH-CH(CH₃)₂ | H | — | 3-Cl-4-CF₃-phenyl |
| -CH-CH(CH₃)₂ | H | — | 3,4,5-trichlorophenyl |
| -CH-CH(CH₃)₂ | H | — | 3-CH₃-4-Cl-phenyl |
| -CH-CH(CH₃)₂ | H | — | 3-Cl-4-CF₃-phenyl |
| -CH-CH(CH₃)₂ | H | -CH₂- | 4-OCF₃-phenyl |
| -CH-CH(CH₃)₂ | H | -CH₂- | 4-CF₃-phenyl |
| -CH-CH(CH₃)₂ | H | -CH₂- | 3-Cl-4-OCF₃-phenyl |
| -CH-CH(CH₃)₂ | H | -(CH₂)₂- | 4-CF₃-phenyl |
| -CH-CH(CH₃)₂ | H | -(CH₂)₂- | 2-CF₃-phenyl |
| -CH-CH(CH₃)₂ | H | -(CH₂)₂- | 4-OCF₃-phenyl |
| -CH-CH₂-phenyl | H | — | 4-CF₃-phenyl |
| -CH-CH₂-phenyl | H | — | 4-OCF₃-phenyl |
| -CH-CH₂-phenyl | H | — | 3-CH₃-4-Cl-phenyl |
| -CH-CH₂-phenyl | H | — | 4-F-phenyl |
| -CH-CH₂-phenyl | H | — | 3,5-dichlorophenyl |
| -CH-CH₂-phenyl | H | — | 3-Cl-4-CF₃-phenyl |
| -CH-CH₂-phenyl | H | — | 3,4,5-trichlorophenyl |
| -CH-CH₂-phenyl | H | — | 4-CH₃-3-Cl-phenyl |
| -CH-CH₂-phenyl | H | — | 3-Cl-4-CF₃-phenyl |

-continued (I)
Structure: Cl-C=C(Cl) with two C=O groups forming maleimide ring, N-A¹-C(=O)-N(R)(A²)ₙ-Ar

| A¹ | R | (A²)ₙ | Ar |
|---|---|---|---|
| -CH(CH₂-phenyl)- | H | -CH₂- | 4-OCF₃-phenyl |
| -CH(CH₂-phenyl)- | H | -CH₂- | 4-CF₃-phenyl |
| -CH(CH₂-phenyl)- | H | -CH₂- | 3-Cl,4-OCF₃-phenyl |
| -CH(CH₂-phenyl)- | H | -(CH₂)₂- | 4-CF₃-phenyl |
| -CH(CH₂-phenyl)- | H | -(CH₂)₂- | 2-CF₃-phenyl |
| -CH(CH₂-phenyl)- | H | -(CH₂)₂- | 4-OCF₃-phenyl |
| -CH(phenyl)- | H | — | 4-CF₃-phenyl |
| -CH(phenyl)- | H | — | 4-OCF₃-phenyl |
| -CH(phenyl)- | H | — | 3-CH₃,4-Cl-phenyl |
| -CH(phenyl)- | H | — | 4-F-phenyl |

-continued (I)
Structure: Cl-C=C(Cl) with two C=O groups forming maleimide ring, N-A¹-C(=O)-N(R)(A²)ₙ-Ar

| A¹ | R | (A²)ₙ | Ar |
|---|---|---|---|
| -CH(phenyl)- | H | — | 3,5-diCl-phenyl |
| -CH(phenyl)- | H | — | 3-Cl,4-CF₃-phenyl |
| -CH(phenyl)- | H | — | 3,4,5-triCl-phenyl |
| -CH(phenyl)- | H | — | 3-Cl,4-CH₃-phenyl |
| -CH(phenyl)- | H | — | 3-Cl,4-CF₃-phenyl |
| -CH(phenyl)- | H | -CH₂- | 4-OCF₃-phenyl |
| -CH(phenyl)- | H | -CH₂- | 4-CF₃-phenyl |
| -CH(phenyl)- | H | -CH₂- | 3-Cl,4-OCF₃-phenyl |
| -CH(phenyl)- | H | -(CH₂)₂- | 4-CF₃-phenyl |

-continued
(I)
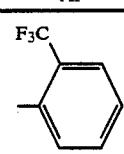
| $A^1$ | R | $(A^2)_n$ | Ar |
|---|---|---|---|
| 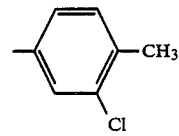 | H | —(CH$_2$)$_2$— | 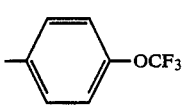 |
| 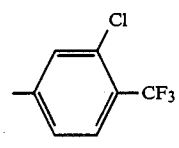 | H | —(CH$_2$)$_2$— | 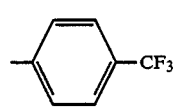 |
| —(CH$_2$)$_4$— | H | — | 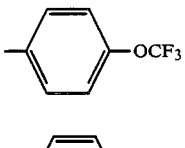 |
| —(CH$_2$)$_4$— | H | — | 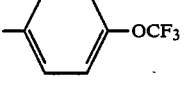 |
| —(CH$_2$)$_4$— | H | — | 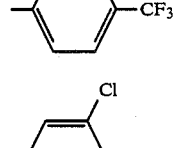 |
| —(CH$_2$)$_4$— | H | — | 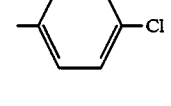 |
| —(CH$_2$)$_4$— | H | — | 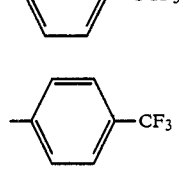 |
| —(CH$_2$)$_4$— | H | — | 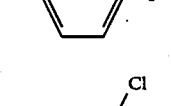 |
| —(CH$_2$)$_4$— | H | — | 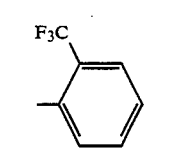 |
-continued
(I)
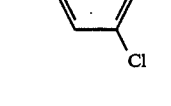
| $A^1$ | R | $(A^2)_n$ | Ar |
|---|---|---|---|
| —(CH$_2$)$_4$— | H | — | 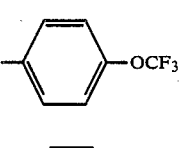 |
| —(CH$_2$)$_4$— | H | — | 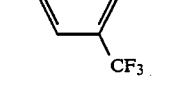 |
| —(CH$_2$)$_4$— | H | —CH$_2$— | 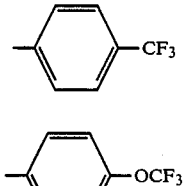 |
| —(CH$_2$)$_4$— | H | —CH$_2$— | 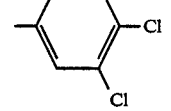 |
| —(CH$_2$)$_4$— | H | —CH$_2$— | 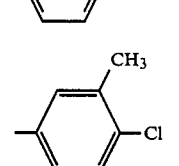 |
| —(CH$_2$)$_4$— | H | —(CH$_2$)$_2$— |  |
| —(CH$_2$)$_4$— | H | —(CH$_2$)$_2$— |  |
| —(CH$_2$)$_4$— | H | —(CH$_2$)$_2$— | 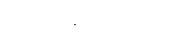 |
| —(CH$_2$)$_5$— | H | — | |
| —(CH$_2$)$_5$— | H | — | |
| —(CH$_2$)$_5$— | H | — | |

-continued

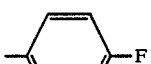

| A¹ | R | (A²)ₙ | Ar |
|---|---|---|---|
| —(CH₂)₅— | H | — | 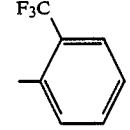 4-F-phenyl |
| —(CH₂)₅— | H | — | 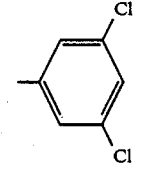 3,5-diCl-phenyl |
| —(CH₂)₅— | H | — | 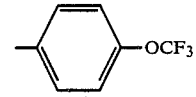 3-Cl-4-CF₃-phenyl |
| —(CH₂)₅— | H | — | 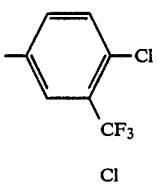 3,4,5-triCl-phenyl |
| —(CH₂)₅— | H | — | 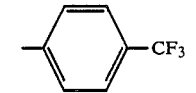 3-CH₃-4-Cl-phenyl |
| —(CH₂)₅— | H | — | 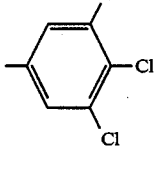 3-Cl-4-CF₃-phenyl |
| —(CH₂)₅— | H | —CH₂— | 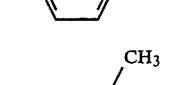 4-OCF₃-phenyl |
| —(CH₂)₅— | H | —CH₂— | 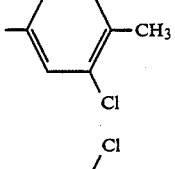 4-CF₃-phenyl |
| —(CH₂)₅— | H | —CH₂— | 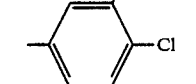 3-Cl-4-OCF₃-phenyl |
| —(CH₂)₅— | H | —(CH₂)₂— | 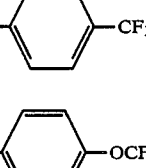 4-CF₃-phenyl |

-continued

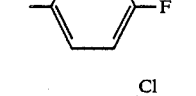

| A¹ | R | (A²)ₙ | Ar |
|---|---|---|---|
| —(CH₂)₅— | H | —(CH₂)₂— | 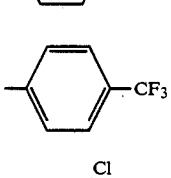 2-CF₃-phenyl |
| —(CH₂)₅— | H | —(CH₂)₂— | 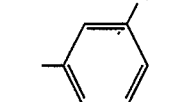 4-OCF₃-phenyl |
| —(CH₂)₆— | H | — | 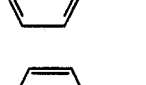 4-CF₃-phenyl |
| —(CH₂)₆— | H | — | 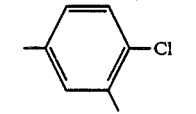 4-OCF₃-phenyl |
| —(CH₂)₆— | H | — | 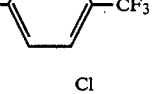 3-CH₃-4-Cl-phenyl |
| —(CH₂)₆— | H | — | 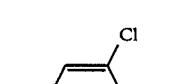 4-F-phenyl |
| —(CH₂)₆— | H | — | 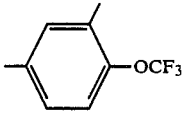 3,5-diCl-phenyl |
| —(CH₂)₆— | H | — | 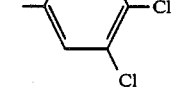 3-Cl-4-CF₃-phenyl |
| —(CH₂)₆— | H | — | 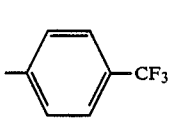 3,4,5-triCl-phenyl |
| —(CH₂)₆— | H | — | 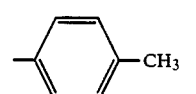 4-CH₃-3-Cl-phenyl |

-continued $$\text{(I)}$$

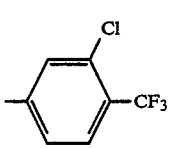

| $A^1$ | R | $(A^2)_n$ | Ar |
|---|---|---|---|
| —(CH$_2$)$_6$— | H | — | 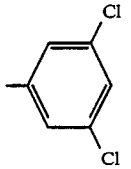 |
| —(CH$_2$)$_6$— | H | —CH$_2$— | 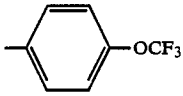 |
| —(CH$_2$)$_6$— | H | —CH$_2$— | 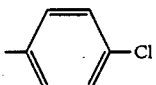 |
| —(CH$_2$)$_6$— | H | —CH$_2$— | 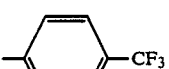 |
| —(CH$_2$)$_6$— | H | —(CH$_2$)$_2$— | 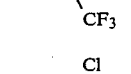 |
| —(CH$_2$)$_6$— | H | —(CH$_2$)$_2$— | 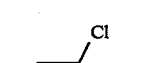 |
| —(CH$_2$)$_6$— | H | —(CH$_2$)$_2$— | 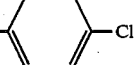 |
| —CH—CH$_2$—<br>            CH$_3$ | H | — | 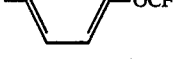 |
| —CH—CH$_2$—<br>            CH$_3$ | H | — | 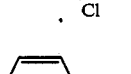 |
| —CH—CH$_2$—<br>            CH$_3$ | H | — | 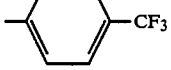 |
| —CH—CH$_2$—<br>            CH$_3$ | H | — | 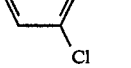 |

-continued $$\text{(I)}$$

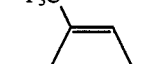

| $A^1$ | R | $(A^2)_n$ | Ar |
|---|---|---|---|
| —CH—CH$_2$—<br>            CH$_3$ | H | — | 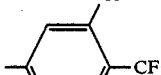 |
| —CH—CH$_2$—<br>            CH$_3$ | H | — | 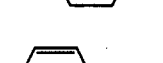 |
| —CH—CH$_2$—<br>            CH$_3$ | H | — | 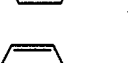 |
| —CH—CH$_2$—<br>            CH$_3$ | H | — | 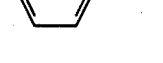 |
| —CH—CH$_2$—<br>            CH$_3$ | H | — | 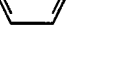 |
| —CH—CH$_2$—<br>            CH$_3$ | H | —CH$_2$— | 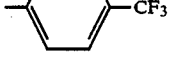 |
| —CH—CH$_2$—<br>            CH$_3$ | H | —CH$_2$— | 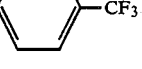 |
| —CH—CH$_2$—<br>            CH$_3$ | H | —(CH$_2$)$_2$— | 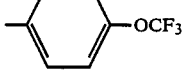 |
| —CH—CH$_2$—<br>            CH$_3$ | H | —(CH$_2$)$_2$— | 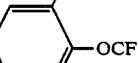 |

-continued $$\text{Structure (I): chloromaleimide-N-A}^1\text{-C(=O)-N(R)-(A}^2)_n\text{-Ar}$$

| A¹ | R | (A²)ₙ | Ar |
|---|---|---|---|
| -CH-CH₂- with CH₃ | H | -(CH₂)₂- | 4-OCF₃-C₆H₄- |
| -(CH₂)₅- | H | — | 3,4-diCl-C₆H₃- |
| -(CH₂)₅- | H | — | 4-Cl-C₆H₄- |
| -(CH₂)₅- | H | — | 3,5-diCl-C₆H₃- |
| -(CH₂)₅- | H | — | 4-CH₃-C₆H₄- |
| -(CH₂)₅- | H | — | 3-Cl-4-OCH₃-C₆H₃- |
| -(CH₂)₅- | H | -CH₂- | 4-Cl-C₆H₄- |
| -(CH₂)₅- | H | -CH₂- | 4-CH₃-C₆H₄- |
| -(CH₂)₅- | H | -(CH₂)₂- | 4-Cl-C₆H₄- |
| -(CH₂)₅- | H | -(CH₂)₂- | 4-CH₃-C₆H₄- |
| -(CH₂)₄- | H | — | 4-CH₃-C₆H₄- |
| -(CH₂)₄- | H | — | 4-OCH₃-C₆H₄- |
| -(CH₂)₄- | H | — | 3-Cl-4-OCH₃-C₆H₃- |
| -(CH₂)₄- | H | -(CH₂)₂- | 4-Cl-C₆H₄- |
| -(CH₂)₄- | H | -(CH₂)₂- | 4-CH₃-C₆H₄- |
| -(CH₂)₆- | H | — | 3,4-diCl-C₆H₃- |
| -(CH₂)₆- | H | — | 4-Cl-C₆H₄- |
| -(CH₂)₆- | H | — | 3,5-diCl-C₆H₃- |
| -(CH₂)₆- | H | — | 4-CH₃-C₆H₄- |
| -(CH₂)₆- | H | — | 4-OCH₃-C₆H₄- |
| -(CH₂)₆- | H | — | 3-Cl-4-OCH₃-C₆H₃- |

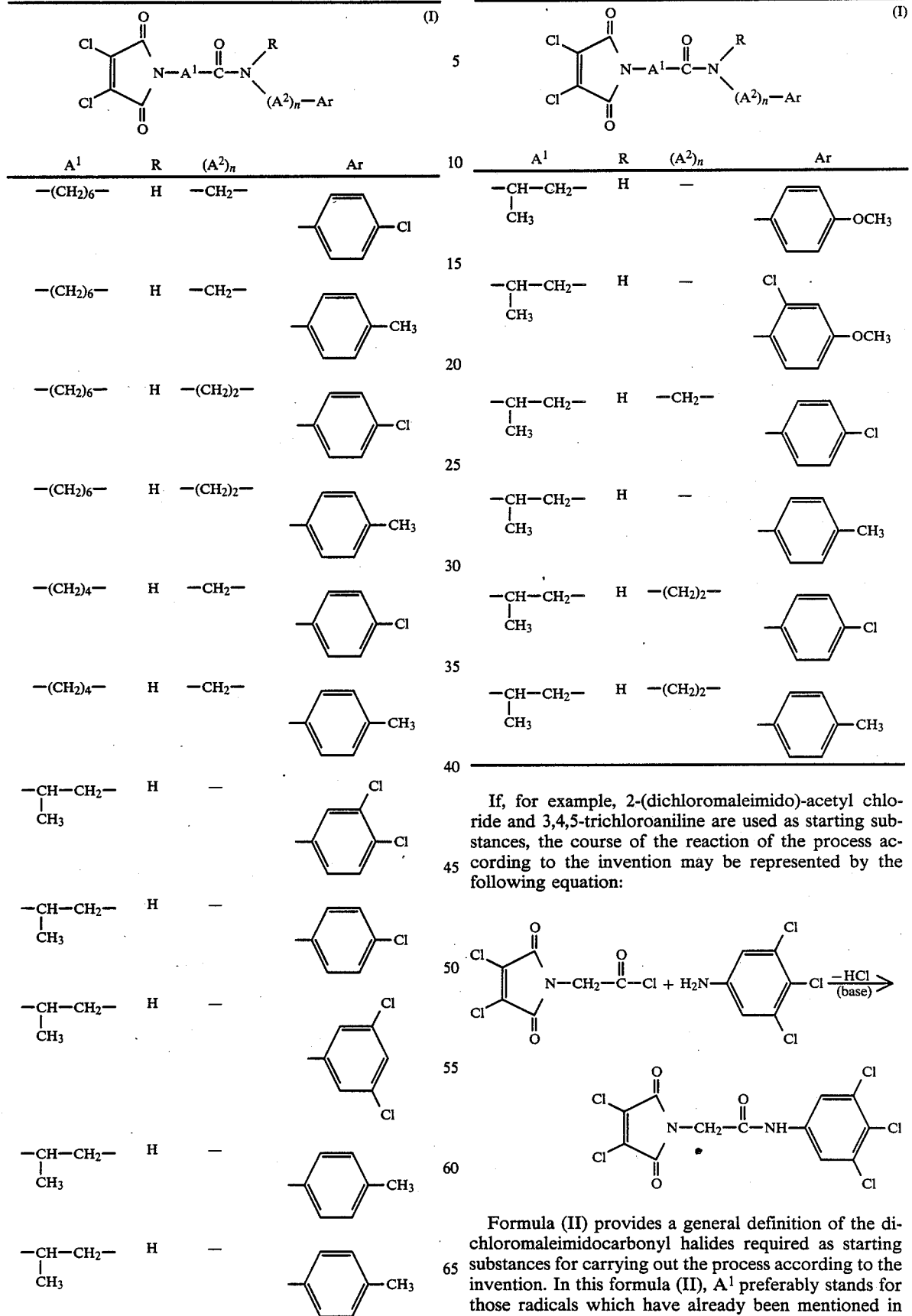

formula (I) according to the invention as being preferred for this substituent.

Hal preferably stands for chlorine or bromine.

Some of the dichloromaleimidocarbonyl halides of the formula (II) are known (cf. CH 617,320 dated 30.05.1980). They are obtained in analogy with known processes when dichloromaleic anhydride of the formula (IV)

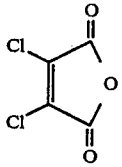

is reacted with amino acids of the formula (V)

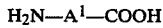

in which

A¹ has the abovementioned meaning, at temperatures between 30° C. and 150° C. and if appropriate in the presence of a diluent, such as, for example, glacial acetic acid, and the resultant dichloromaleimidocarboxylic acids of the formula (VI)

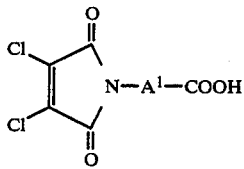

in which

A¹ has the abovementioned meaning, are reacted in a customary manner with halogenating agents, such as, for example, phosphorus pentachloride, phosphorus tribromide, phosphorus oxychloride or thionyl chloride, at temperatures between 30° C. and 150° C.

Most of the dichloromaleimidocarboxylic acids of the formula (VI) are known (cf. J. Prakt. Chem. 327, 857–864 [1985]).

Dichloromaleic anhydride of the formula (IV) has been disclosed (cf., for example, DE-OS (German Published Specification) 1,290,555 or U.S. Pat. No. 3,297,722).

Amino acids of the formula (V) are generally known compounds of organic chemistry.

Formula (III) provides a general definition of the amines furthermore required as starting substances for carrying out the process according to the invention. In this formula (III), R, Ar, A² and n preferably stand for those radicals and indices which have already been mentioned in connection with the description of the substances of the formula (I) according to the invention as being preferred for these substituents and indices.

The amines of the formula (III) are also generally known compounds of organic chemistry.

Suitable diluents for carrying out the process according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

The process according to the invention is preferably carried out in the presence of a suitable acid-binding agent. Suitable compounds are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out the process according to the invention, the reaction temperatures may be varied within a relatively wide range. In general, the process is carried out at temperatures between 0° C. and 150° C., preferably at temperatures between 20° C. and 120° C.

For carrying out the process according to the invention, 1.0 to 2.5 moles, preferably 1.0 to 1.5 moles, of amine of the formula (III) and if appropriate 1.0 to 2.5 moles, preferably 1.0 to 1.5 mole, of acid-binding agent are generally employed per mole of dichloromaleimidocarbonyl halide of the formula (II). The reaction is carried out and the reaction products are worked up and isolated by generally customary methods.

The active substances according to the invention exhibit a strong action against pests and can be employed in practice for combating undesired harmful organisms. The active substances can be used as pesticides, in particular fungicides and bactericides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris* pv. oryzae; Pseudomonas species, such as, for example, *Pseudomonas syringae* pv. lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginiea;* Podosphaera species, such as, for example, *Podosphaera leucotrichia;* Venturia species, such as, for example, *Venturia inaequalis;* Pyrenophora species, such as, for example, *Pyrenophora teres* or *P. graminea* (conidia form: Drechslera, syn: Helminthosporium): Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be employed with particularly good success in the combating of diseases in viticulture, fruit growing and vegetable growing, such as, for example, against the causative organism of powdery mildew of grapevine (*Plasmopara viticola*) or against the causative organism of apple scab (*Venturia inaequalis*), or for combating of seed-borne pathogens of soya bean (for example *Rhizoctonia solani,* Fusarium sp., Pythium sp.), or for combating of rice diseases, such as, for example, against the causative organism of rice blast disease (*Pyricularia oryzae*). The systemic properties of the compounds according to the invention facilitate their application as seed dressing agents.

Furthermore, the active compounds according to the invention also possess bactericidal properties.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolyzation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, or as a mixture with fertilizers and growth regulators.

The active compounds can be applied as such, in the form of their formulations or in use forms prepared therefrom, such as ready-to-use solutions, suspensions, wettable powders, pastes, soluble powders, dusts and granules. Application is carried out in the customary manner, for example by watering, spraying, atomizing, scattering, dusting, foaming, brushing on etc. Furthermore, it is possible to apply the active compounds using the ultra-low-volume method or to inject the active compound formulation or the active compound itself into the soil. The seeds of the plant can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.2% by weight, are required at the place of action.

PREPARATION EXAMPLES

Example 1

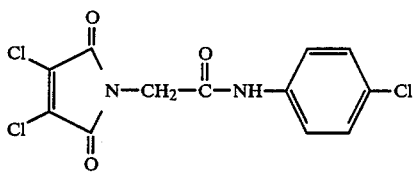

A mixture consisting of 3.5 g (0.027 mol) of p-chloroaniline and 3.45 ml (0.025 mol) of triethylamine in 40 ml of dioxane is added dropwise and with stirring to 6.0 g (0.025 mol) of 2-chloromaleimidoacetyl chloride in 60 ml of dioxane, during which operation the temperature of the reaction mixture increases to 40° C. When the addition is complete, the mixture is stirred at room temperature for 4 hours and poured into 1N hydrochloric acid, and the resultant precipitate is filtered off by suction, washed with saturated aqueous sodium hydrogen carbonate solution and water, and dried at 50° C. in vacuo.

7.1 g (96% of theory) of 2-(dichloromaleimido)-N-(4-chlorophenyl)-acetamide of melting point 212° C.–214° C. are obtained.

Preparation of the starting compound

Example II-1

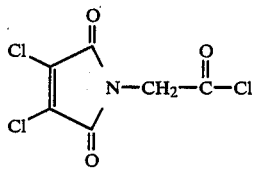

60 ml (0.81 mol) of thionyl chloride are added to 70 g (0.31 mol) of 2-(dichloromaleimido)-acetic acid, the mixture is refluxed for 16 hours and evaporated in vacuo, the residue is taken up in absolute toluene, and the solvent and remaining thionyl chloride are removed in vacuo.

75.1 g (99% of theory) of 2-(dichloromaleimido)acetyl chloride of melting point 102° C.–103° C. are obtained.

Example VI-1

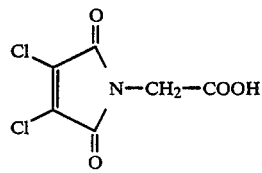

A suspension of 75 g (1.0 mol) of glycine in 400 ml of glacial acetic acid is added to 167 g (1 mol) of dichloromaleic anhydride in 1,000 ml of glacial acetic acid, the mixture is refluxed for one hour and cooled, and the resultant precipitate is filtered off by suction, washed with 2.5 l of water and dried at 50° C. in vacuo.

139.9 g (63% of theory) of 2-(dichloromaleimido)-acetic acid of melting point 191° C.–192° C. are obtained.

The following N-substituted dichloromaleimides of the general formula (I) are obtained in a corresponding manner and in accordance with the general instructions for the preparation:

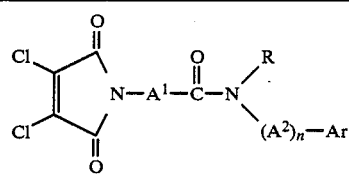

(I)

| Ex-No. | $A^1$ | R | $(A^2)_n$ | Ar | Melting point |
|---|---|---|---|---|---|
| 2 | —CH$_2$— | H | — | ![3,4-dichlorophenyl] | 218–220° C. |
| 3 | —CH$_2$— | H | — | ![4-methylphenyl] | 213–215° C. |
| 4 | —CH$_2$— | H | — | ![3-chlorophenyl] | 193–194° C. |

-continued
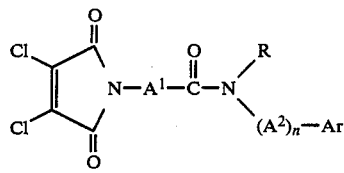
(I)
| Ex-No. | $A^1$ | R | $(A^2)_n$ | Ar | Melting point |
|---|---|---|---|---|---|
| 5 | —CH₂— | H | — | ⌬—OCH₃ (4-methoxyphenyl) | 211–213° C. |
| 6 | —CH₂— | H | — | 2-chlorophenyl | 186–188° C. |
| 7 | —CH₂— | H | — | 3,5-dichlorophenyl | 233–235° C. |
| 8 | —CH₂— | H | — | 4-fluorophenyl | 177–178° C. |
| 9 | —CH—CH(CH₃)₂ | H | — | 3,5-dichlorophenyl | 169–171° C. |
| 10 | —CH—CH(CH₃)₂ | H | — | 4-fluorophenyl | ¹H-NMR*: 4,35–4,45 (1H) |
| 11 | —CH—CH(CH₃)₂ | H | — | 2-chlorophenyl | 89–91° C. |
| 12 | —CH—CH(CH₃)₂ | H | — | 4-methoxyphenyl | 116–118° C. |
| 13 | —CH—CH(CH₃)₂ | H | — | 3-chlorophenyl | 140–141° C. |
| 14 | —CH—CH(CH₃)₂ | H | — | 4-methylphenyl | 70–71° C. |

-continued
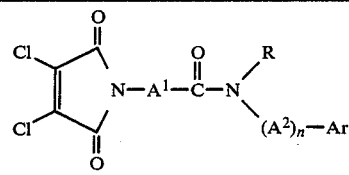
| Ex-No. | $A^1$ | R | $(A^2)_n$ | Ar | Melting point |
|---|---|---|---|---|---|
| 15 | -CH-<br>CH(CH₃)₂ | H | — | 3,4-di-Cl-phenyl | ¹H-NMR*:<br>4,3–4,4<br>(1H) |
| 16 | -CH-<br>CH(CH₃)₂ | H | — | 4-Cl-phenyl | 135–138° C. |
| 17 | -CH-<br>CH(CH₃)₂ | H | — | phenyl | 146–148° C. |
| 18 | -CH₂- | CH₃ | — | phenyl | 193–195° C. |
| 19 | -CH₂- | H | — | 2,3-di-Cl-phenyl | 216° C. |
| 20 | -CH₂- | H | — | 2,4-di-Cl-phenyl | 208° C. |
| 21 | -CH₂- | H | — | 2-CF₃-4-Cl-phenyl | 174–177° C. |
| 22 | -CH₂- | H | — | 3,4-di-CF₃-phenyl | 158° C. |
| 23 | -CH₂- | H | — | 2-CF₃-4-NO₂-phenyl | 189–192° C. |
| 24 | -CH₂- | H | — | 2,5-di-Cl-phenyl | 230° C. |

-continued
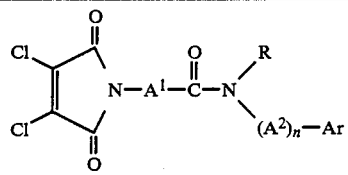
(I)
| Ex-No. | A¹ | R | (A²)ₙ | Ar | Melting point |
|---|---|---|---|---|---|
| 25 | —CH₂— | H | — | 2,4,5-trichlorophenyl | 220° C. |
| 26 | —CH₂— | H | — | 3,4,5-trichlorophenyl | 237° C. |
| 27 | —CH₂— | H | — | 3-methylphenyl | 222° C. |
| 28 | —CH₂— | H | — | 3-chloro-4-methylphenyl | 213° C. |
| 29 | —CH₂— | H | —CH₂— | phenyl | 173–175° C. |
| 30 | —CH₂— | H | —CH₂— | 4-chlorophenyl | 192–194° C. |
| 31 | —CH₂— | H | — | 2-methyl-4-chlorophenyl | 217–218° C. |
| 32 | —CH₂— | H | —CH₂— | 4-methoxyphenyl | 161–163° C. |
| 33 | —CH₂— | H | —CH(CH₃)— | phenyl | 172–173° C. |
| 34 | —CH₂— | H | —(CH₂)₂— | phenyl | 170–171° C. |

-continued

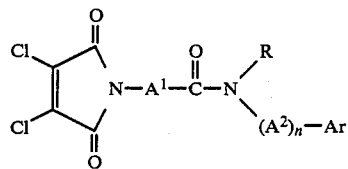
(I)

| Ex-No. | $A^1$ | R | $(A^2)_n$ | Ar | Melting point |
|---|---|---|---|---|---|
| 35 | —CH$_2$— | H | — | 2,4-(CH$_3$)$_2$-C$_6$H$_3$— | >220° C. |
| 36 | —CH(CH$_2$—C$_6$H$_5$)— | H | — | C$_6$H$_5$— | 183–184° C. (L-Form) |
| 37 | —CH(CH$_2$—C$_6$H$_5$)— | H | — | 4-Cl-C$_6$H$_4$— | 235–236° C. (L-Form) |
| 38 | —CH(CH$_2$—C$_6$H$_5$)— | H | — | 4-CH$_3$-C$_6$H$_4$— | 183–184° C. (L-Form) |
| 39 | —CH(CH$_2$—C$_6$H$_5$)— | H | — | 4-OCH$_3$-C$_6$H$_4$— | 178–180° C. (L-Form) |
| 40 | —CH(CH$_2$—C$_6$H$_5$)— | H | — | 3,4-Cl$_2$-C$_6$H$_3$— | 199–200° C. (L-Form) |
| 41 | —CH(CH$_2$—C$_6$H$_5$)— | H | —CH$_2$— | C$_6$H$_5$— | 163–164° C. (L-Form) |
| 42 | —CH(CH$_2$—C$_6$H$_5$)— | H | —CH$_2$— | 4-Cl-C$_6$H$_4$— | 143–144° C. (L-Form) |
| 43 | —CH$_2$— | H | — | 3,5-(CF$_3$)$_2$-C$_6$H$_3$— | 206–208° C. |
| 44 | —CH$_2$— | H | — | 4-C(CH$_3$)$_3$-C$_6$H$_4$— | 206–207° C. |

-continued
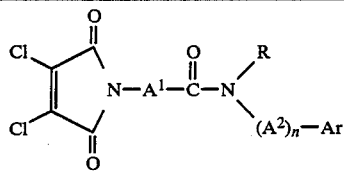
(I)
| Ex-No. | $A^1$ | R | $(A^2)_n$ | Ar | Melting point |
|---|---|---|---|---|---|
| 45 | —CH$_2$— | H | — | 4-F, 3-CF$_3$-phenyl | 194–196° C. |
| 46 | —CH$_2$— | H | — | 2-F-phenyl | 180–182° C. |
| 47 | —CH$_2$— | H | — | 4-Cl, 2-F-phenyl | 204–205° C. |
| 48 | —CH$_2$— | H | — | 4-SCH$_3$, 3-CF$_3$-phenyl | 180–182° C. |
| 49 | —CH$_2$— | H | — | 3-F, 2,4-Cl$_2$-phenyl | 208–210° C. |
| 50 | —CH$_2$— | H | — | 3-Cl, 4-CF$_3$-phenyl | 189–190° C. |
| 51 | —CH$_2$— | H | — | 4-SCF$_3$-phenyl | 180–182° C. |
| 52 | —CH$_2$— | H | — | 4-OCF$_3$-phenyl | 174–176° C. |
| 53 | —CH$_2$— | H | — | 3-Cl, 4-OCH$_3$-phenyl | 180–182° C. |
| 54 | —CH$_2$— | H | — | 3-Cl, 4-F-phenyl | 194° C. |

-continued
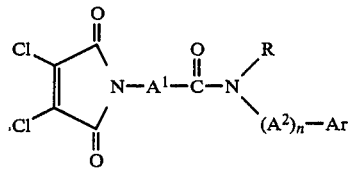
(I)
| Ex-No. | $A^1$ | R | $(A^2)_n$ | Ar | Melting point |
|---|---|---|---|---|---|
| 55 | —CH$_2$— | H | — | 2-F, 3-Cl, 4-F phenyl | 189–190° C. |
| 56 | —CH$_2$— | H | — | 3-Cl, 4-SCF$_3$ phenyl | 152° C. |
| 57 | —CH$_2$— | H | —CH$_2$— | 2,6-diF phenyl | 199° C. |
| 58 | —CH$_2$— | H | —CH$_2$— | 3-CF$_3$ phenyl | 172° C. |
| 59 | —CH$_2$— | H | — | 2-Cl, 3-CF$_3$, 5-CF$_3$ phenyl | 230° C. |
| 60 | —CH$_2$— | H | —CH$_2$— | 4-CH$_3$ phenyl | 181° C. |
| 61 | —CH$_2$— | H | —CH$_2$— | 4-OCF$_3$ phenyl | 184° C. |
| 62 | —CH$_2$— | H | —CH$_2$— | 3-Cl, 4-OCF$_3$ phenyl | 210° C. |
| 63 | —CH$_2$— | H | —(CH$_2$)$_2$— | 4-CF$_3$ phenyl | 179° C. |

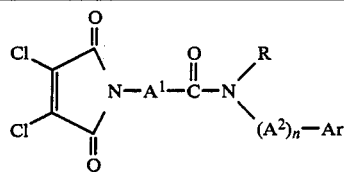
(I)
| Ex-No. | $A^1$ | R | $(A^2)_n$ | Ar | Melting point |
|---|---|---|---|---|---|
| 64 | —CH$_2$— | H | —(CH$_2$)$_2$— | 2-CF$_3$-C$_6$H$_4$— | 185° C. |
| 65 | —CH$_2$— | H | —(CH$_2$)$_2$— | 4-OCF$_3$-C$_6$H$_4$— | 160–162° C. |
| 66 | —CH(CH$_3$)— | H | —CH$_2$— | C$_6$H$_5$— | 96° C. (L-Form) |
| 67 | —CH(CH$_3$)— | H | —CH$_2$— | 4-CH$_3$-C$_6$H$_4$— | 142–143° C. (L-Form) |
| 68 | —CH(CH$_3$)— | H | — | C$_6$H$_5$— | 183–184° C. |
| 69 | —CH(CH$_3$)— | H | — | 4-Cl-C$_6$H$_4$— | 181° C. (L-Form) |
| 70 | —CH(CH$_3$)— | H | — | 4-OCH$_3$-C$_6$H$_4$— | 159–162° C. (L-Form) |
| 71 | —CH(CH$_3$)— | H | — | 4-CH$_3$-C$_6$H$_4$— | 194–195° C. (L-Form) |
| 72 | —CH(CH$_3$)— | H | — | 3,4-Cl$_2$-C$_6$H$_3$— | 65° C. (L-Form) |
| 73 | —CH$_2$—CH$_2$— | H | — | C$_6$H$_5$— | 197–198° C. |
| 74 | —CH$_2$—CH$_2$— | H | — | 4-Cl-C$_6$H$_4$— | 208–210° C. |

-continued
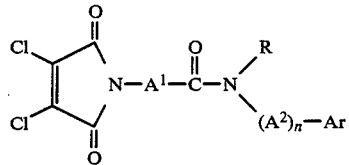
(I)
| Ex-No. | A¹ | R | (A²)ₙ | Ar | Melting point |
|---|---|---|---|---|---|
| 75 | —CH₂—CH₂— | H | — | 4-OCH₃-C₆H₄— | 188–189° C. |
| 76 | —CH₂—CH₂— | H | — | 4-CH₃-C₆H₄— | 190–191° C. |
| 77 | —CH₂—CH₂— | H | — | 3,4-Cl₂-C₆H₃— | 191° C. |
| 78 | —CH₂—CH₂— | H | —CH₂— | C₆H₅— | 171–172° C. |
| 79 | —CH₂—CH₂— | H | —CH₂— | 4-Cl-C₆H₄— | 177–178° C. |
| 80 | —CH(CH₃)— | H | — | C₆H₅— | 173° C. (D,L-Form) |
| 81 | —CH(CH₃)— | H | — | 4-Cl-C₆H₄— | 168–170° C. (D,L-Form) |
| 82 | —(CH₂)₃— | H | — | 4-Cl-C₆H₄— | 160–162° C. |
| 83 | —CH₂— | CH₃ | — | 4-CH₃-C₆H₄— | 121–122° C. |
| 84 | —(CH₂)₃— | H | — | C₆H₅— | 139–140° C. |
| 85 | —(CH₂)₃— | H | — | 4-CH₃-C₆H₄— | 166° C. |

-continued
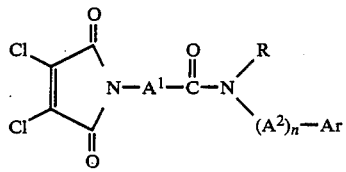
(I)
| Ex-No. | $A^1$ | R | $(A^2)_n$ | Ar | Melting point |
|---|---|---|---|---|---|
| 86 | —(CH$_2$)$_3$— | H | — | —C$_6$H$_4$-OCH$_3$ (para) | 158° C. |
| 87 | —(CH$_2$)$_3$— | H | — | 3,4-dichlorophenyl | 156–158° C. |
| 88 | —(CH$_2$)$_3$— | H | —CH$_2$— | phenyl | 150–152° C. |
| 89 | —(CH$_2$)$_3$— | H | —CH$_2$— | 4-chlorophenyl | 186–187° C. |
| 90 | —C(CH$_3$)$_2$— | H | — | phenyl | 201–203° C. |
| 91 | —C(CH$_3$)$_2$— | H | — | 4-chlorophenyl | 199–200° C. |
| 92 | —C(CH$_3$)$_2$— | H | — | 4-methylphenyl | 198° C. |
| 93 | —C(CH$_3$)$_2$— | H | — | 4-methoxyphenyl | 161–163° C. |
| 94 | —C(CH$_3$)$_2$— | H | — | 3,4-dichlorophenyl | 74–76° C. |
| 95 | —C(CH$_3$)$_2$— | H | —CH$_2$— | 4-chlorophenyl | 164° C. |
| 96 | —CH(CH$_2$—C$_6$H$_5$)— | H | — | phenyl | 211–212° C. (D,L-Form) |

-continued

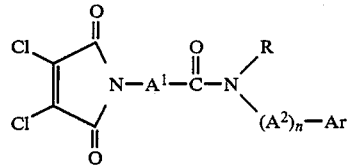
(I)

| Ex-No. | A¹ | R | (A²)ₙ | Ar | Melting point |
|---|---|---|---|---|---|
| 97 | −CH−<br>│<br>CH₂−C₆H₅ | H | — | −⟨4-Cl-C₆H₄⟩ | 219° C.<br>(D,L-Form) |
| 98 | −CH−<br>│<br>CH₂−C₆H₅ | H | — | −⟨4-CH₃-C₆H₄⟩ | 181° C.<br>(D,L-Form) |
| 99 | −CH−<br>│<br>CH₂−C₆H₅ | H | — | −⟨4-OCH₃-C₆H₄⟩ | 182–183° C.<br>(D,L-Form) |
| 100 | −CH−<br>│<br>CH₂−C₆H₅ | H | — | −⟨3,4-Cl₂-C₆H₃⟩ | 197° C.<br>(D,L-Form) |
| 101 | −CH−<br>│<br>CH₂−C₆H₅ | H | −CH₂− | −C₆H₅ | 186–187° C.<br>(D,L-Form) |
| 102 | −CH−<br>│<br>CH₂−C₆H₅ | H | −CH₂− | −⟨4-Cl-C₆H₄⟩ | 158° C.<br>(D,L-Form) |
| 103 | −CH−<br>│<br>C₆H₅ | H | — | −⟨4-OCH₃-C₆H₄⟩ | 157–158° C. |
| 104 | −CH−<br>│<br>C₆H₅ | H | — | −⟨3,4-Cl₂-C₆H₃⟩ | 144–146° C. |
| 105 | −CH−<br>│<br>C₆H₅ | H | −CH₂− | −C₆H₅ | 145° C. |
| 106 | −CH−<br>│<br>C₆H₅ | H | −CH₂− | −⟨4-Cl-C₆H₄⟩ | 190–191° C. |
| 107 | −CH₂− | H | −CH−<br>│<br>CH₃ | −⟨4-Cl-C₆H₄⟩ | 175° C. |

-continued
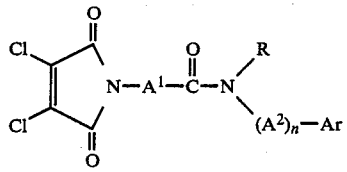
(I)
| Ex-No. | $A^1$ | R | $(A^2)_n$ | Ar | Melting point |
|---|---|---|---|---|---|
| 108 | —CH₂—CH₂— | H | — | 4-CF₃-C₆H₄ | 208–210° C. |
| 109 | —CH₂—CH₂— | H | —CH₂—CH₂— | 4-CF₃-C₆H₄ | 162–164° C. |
| 110 | —CH₂—CH₂— | H | —CH₂—CH₂— | 2-CF₃-C₆H₄ | 131° C. |
| 111 | —CH₂—CH₂— | H | —CH₂—CH₂— | 4-OCF₃-C₆H₄ | 159–161° C. |
| 112 | —CH₂—CH₂— | H | — | 2-CF₃-4-Cl-C₆H₃ | 130–131° C. |
| 113 | —CH₂—CH₂— | H | —CH₂— | 4-OCF₃-C₆H₄ | 160° C. |
| 114 | —CH₂—CH₂— | H | —CH₂— | 3-Cl-4-OCF₃-C₆H₃ | 134–137° C. |
| 115 | —CH₂—CH₂— | H | — | 2-CH₃-4-Cl-C₆H₃ | 194° C. |
| 116 | —CH₂—CH₂— | H | — | 3,4-Cl₂-C₆H₃ | 181–183° C. |
| 117 | —CH₂—CH₂— | H | — | 3,4,5-Cl₃-C₆H₂ | 208° C. |

-continued
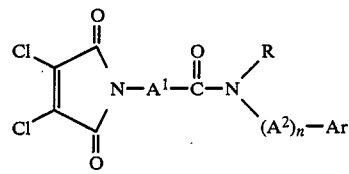
| Ex-No. | A¹ | R | $(A^2)_n$ | Ar | Melting point |
|---|---|---|---|---|---|
| 118 | —CH₂—CH₂— | H | — | 3-Cl, 4-CH₃-phenyl | 179° C. |
| 119 | —(CH₂)₃— | H | — | 4-CF₃-phenyl | 132–134° C. |
| 120 | —(CH₂)₃— | H | — | 4-OCF₃-phenyl | 143° C. |
| 121 | —(CH₂)₃— | H | — | 3-CF₃, 4-Cl-phenyl | 80–82° C. |
| 122 | —(CH₂)₃— | H | —CH₂— | 4-OCF₃-phenyl | 126° C. |
| 123 | —(CH₂)₃— | H | —CH₂— | 3-Cl, 4-OCF₃-phenyl | 118–120° C. |
| 124 | —(CH₂)₃— | H | — | 3-CH₃, 4-Cl-phenyl | 166–167° C. |
| 125 | —CH₂—CH₂— | H | — | 4-OCF₃-phenyl | 183° C. |
| 126 | —CH₂—CH₂— | H | — | 3-Cl, 4-CF₃-phenyl | 199–202° C. |
| 127 | —CH₂—CH₂—CH₂— | H | — | 3,4-diCl-phenyl | 135° C. |

-continued
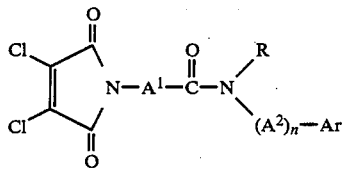
(I)
| Ex-No. | $A^1$ | R | $(A^2)_n$ | Ar | Melting point |
|---|---|---|---|---|---|
| 128 | —CH₂—CH₂—CH₂— | H | —CH₂—CH₂— | 4-OCF₃-C₆H₄— | 132° C. |
| 129 | —CH₂—CH₂—CH₂— | H | — | 3,4,5-trichlorophenyl | 196° C. |
| 130 | —CH₂—CH₂—CH₂— | H | — | 3-Cl-4-CH₃-phenyl | 176° C. |
| 131 | —(CH₂)₅— | H | — | 3,4-dichlorophenyl | 131—133° C. |
| 132 | —(CH₂)₅— | H | — | 4-Cl-phenyl | 149–150° C. |
| 133 | —(CH₂)₅— | H | —CH₂— | 4-Cl-phenyl | 130–139° C. |
| 134 | —CH(CH₃)—CH₂— | H | — | 3,4-dichlorophenyl | 146–148° C. |
| 135 | —CH(CH₃)—CH₂— | H | — | 4-Cl-phenyl | 160–161° C. |
| 136 | —(CH₂)₄— | H | — | 4-Cl-phenyl | 156–157° C. |
| 137 | —CH₂—CH₂— | H | — | 4-F-phenyl | 188° C. |

-continued
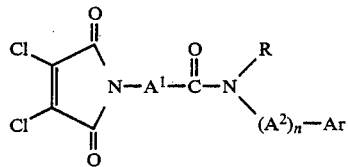
(I)
| Ex-No. | A¹ | R | (A²)ₙ | Ar | Melting point |
|---|---|---|---|---|---|
| 138 | —CH₂—CH₂—CH₂— | H | —CH₂—CH₂— | 4-CF₃-C₆H₄ | 139° C. |
| 139 | —CH₂—CH₂—CH₂— | H | —CH₂—CH₂— | 2-CF₃-C₆H₄ | 106° C. |
| 140 | —CH₂—CH₂—CH₂— | H | — | 4-F-C₆H₄ | 149° C. |
| 141 | —CH₂—CH₂—CH₂— | H | — | 3-Cl-4-CF₃-C₆H₃ | 128° C. |
| 142 | —CH(CH₃)—CH₂— | H | —CH₂— | 4-Cl-C₆H₄ | 171° C. |
| 143 | —CH₂—CH₂—CH₂—CH₂— | H | — | 3,4-Cl₂-C₆H₃ | 140° C. |
| 144 | —CH₂—CH₂—CH₂— | H | —CH₂— | 4-Cl-C₆H₄ | 167° C. |
| 145 | —CH₂—CH₂— | H | —CH₂— | 4-CF₃-C₆H₄ | 177° C. |
| 146 | —CH₂—CH₂—CH₂— | H | —CH₂— | 4-CF₃-C₆H₄ | 132° C. |
| 147 | —CH₂—CH₂—CH₂— | H | —CH(CH₃)— | 4-Cl-C₆H₄ | 136° C. |

-continued

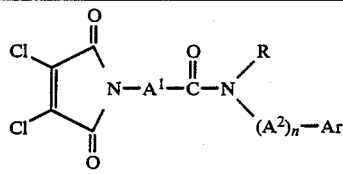

| Ex-No. | $A^1$ | R | $(A^2)_n$ | Ar | Melting point |
|---|---|---|---|---|---|
| 148 | —CH$_2$—CH$_2$— | H | —CH(CH$_3$)— | 4-Cl-C$_6$H$_4$ | 146° C. |

*The $^1$H-NMR spectra wee recorded in deuterochloroform (CDCl$_3$) with tetramethylsilane (TMS) as the internal standard. The data of the chemical shift are expressed as δ-values in ppm.

Use Examples

In the following use examples, the compounds listed below were employed as comparison substances:

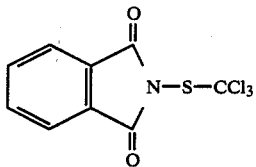

N-Trichloromethanesulphenylphthalimide (folpet)

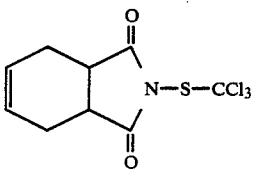

N-Trichloromethanesulphenyltetrahydrophthalimide (captan) Example A

Plasmopara test (vines)/protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and then remain in a humidity chamber at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, the compounds of the Preparation Examples 27, 30, 56, 60, 77, 79 and 95, for example, show a clearly superior activity as compared with the prior art.

Example B

Venturia test (apple)/protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the compounds of Preparation Examples 38, 77, 82 and 87, for example, show a clearly superior activity as compared with the prior art.

Example C

Pyricularia test (rice)/protective

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, the compounds of Preparation Examples 25, 28, 30, 36, 39, 42, 64, 74, 75, 76, 79 and 82, for example, show clearly better activity as compared with untreated control plants.

Example D

Test for soil-borne pathogens (soya bean)/seed treatment field trial

Amount of seed per plot: 30 g
Plot size: 2 m²
Number of replicates: 3
Development stage of the plants at evaluation: 2-leaf The active compounds are applied as dry seed-dressing agents. They are prepared by extending the specific active compound with ground natural minerals to give a finely disperse mixture guaranteeing an even distribution on the surface of the seeds.

For carrying out the seed-dressing, the infected seeds are shaken for 3 minutes in a sealed glass flask together with the seed-dressing agent.

The soil is prepared as is customary in practice, and the seeds are sown in the field at a point in time which is favourable for infection with disease.

Evaluation is carried out at a point in time when the symptoms of diseases are complete and clearly recognizable.

In this test, the compound of Preparation Example 3, for example, has a clearly superior activity as compared with the prior art.

What is claimed is:

1. An N-substituted dichloromaleimide of the formula

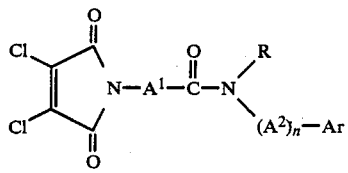

in which
R stands for hydrogen or for alkyl having 1 to 6 carbon atoms,
Ar stands for unsubstituted phenyl or phenyl which is mono-, di- or tri-substituted by non-sterically hindering identical or different substituents selected from the group consisting of halogen; cyano; nitro; alkyl; alkoxy or alkylthio, each having 1 to 4 carbon atoms; halogenoalkyl, halogenoalkoxy, dioxyhalogenoalkylene or halogenoalkylthio, each having 1 to 4 carbon atoms and 1 to 9 identical or different halogen atoms; alkenyl, alkinyl, alkenyloxy or alkinyloxy, each having 3 to 6 carbon atoms; cycloalkyl having 3 to 7 carbon atoms; alkoxycarbonylalkyl or alkoxyalkyl, each having 1 to 4 carbon atoms in the individual alkyl moieties; phenyl, benzyl, phenoxy, benzyloxy, each being unsubstituted or mono-substituted by substituents selected from the group consisting of halogen and alkyl having 1 to 4 carbon atoms,
$A^1$ and $A^2$ independently of one another each stand for unsubstituted or phenyl-substituted, alkylene having 1 to 8 carbon atoms, where the phenyl substituent is unsubstituted or mono-substituted by substituents selected from the group consisting of halogen; alkyl, alkoxy, halogenoalkyl or halogenoalkoxy, each having 1 to 4 carbon atoms, and, in the case of halogenoalkyl or halogenoalkoxy, having 1 to 9 identical or different halogen atoms, and n stands for a number 0 or 1, and pure isomers or isomer mixtures thereof, with the exception of the compound 2-(dichloromaleimido)-acetanilide.

2. An N-substituted dichloromaleimide according to claim 1, in which
R stands for hydrogen or for alkyl having 1 to 4 carbon atoms,
Ar stands for unsubstituted phenyl or phenyl which is mono-, di- or tri-substituted by identical or different non-sterically hindering substituents selected from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoroethoxy, dioxydifluoromethylene, trifluoromethylthio, allyl, propargyl, cyclopropyl, cyclohexyl, phenyl, benzyl, phenoxy and benzloxy,
$A^1$ stands for alkylene which is unsubstituted or substituted by phenyl and which has 1 to 6 carbon atoms,
$A^2$ stands for unsubstituted alkylene having 1 to 6 carbon atoms and n stands for a number 0 to 1, and pure isomers or isomer mixtures thereof, with the exception of the compound 2-(dichloromaleimido)-acetanilide.

3. An N-substituted dichloromaleimide according to claim 1, in which
R stands for hydrogen, methyl or ethyl,
Ar stands for unsubstituted phenyl or phenyl which is mono-, di-, or tri-substituted by identical or different non-sterically hindering substituents selected rom the group consisting of fluorine, chlorine, bromine, cyano, nitro, methyl, ethyl, n- or i-propyl, n-, i-, s- or t-butyl, methoxy, methylthio, trifluoromethyl, trifluoromethoxy, trifluoromethylthio or divalent dioxydifluoromethylene,
$A^1$ stands for alkylene which is unsubstituted or monosubstituted by phenyl and which has 1 to 4 carbon atoms,
$A^2$ stands for alkylene having 1 to 4 carbon atoms and n stands for a number 0 to 1, and pure isomers and isomer mixtures thereof, with the exception of the compound 2-(dichloromaleimido)-acetanilide.

4. A compound according to claim 1 wherein such compound is 2-(dichloromaleimido)-N-(4-methylphenyl)-acetamide of the formula

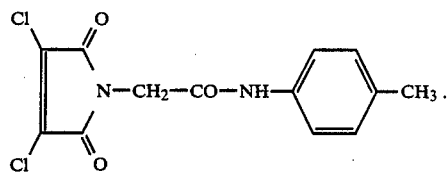

5. A compound according to claim 1 wherein such compound is 2-(dichloromaleimide)-N-(4-methylbenzyl)-acetamide of the formula

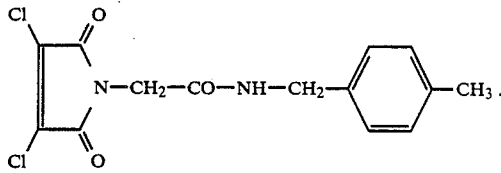

6. A compound according to claim 1 wherein such compound is 3-(dichloromaleimido)-N-(3,4-dichlorophenyl)-propionamide of the formula

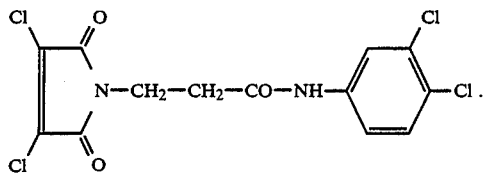

7. A pesticidal composition comprising a pesticidally effective amount of at least one N-substituted dichloromaleimide according to claim 1, and a suitable extender.

8. A fungicial or bactericidal composition comprising an effective amount of at least one N-substituted di-chloromaleimide according to claim 1 and a suitable extender.

9. A method of combating fungi or bacteria comprising applying to said fungi or bacteria or to a locus thereof an effective amount of at least one N-substituted-di-chloromaleimide according to claim 1.

10. A method according to claim 7 wherein such compound is
2-(dichloromaleimido)-N-(4-methylphenyl)-acetamide,
2-(dichloromaleimido)-N-(4-methylbenzyl)-acetamide or
3-(dichloromaleimido)-N-(3,4-dichlorophenyl)-propionamide.

* * * * *